United States Patent
Hagn et al.

(10) Patent No.: US 8,812,160 B2
(45) Date of Patent: Aug. 19, 2014

(54) INPUT APPARATUS FOR MEDICAL MINIMALLY INVASIVE ROBOTS OR MEDICAL SIMULATORS AND MEDICAL DEVICE HAVING AN INPUT APPARATUS

(75) Inventors: Ulrich Hagn, Paehl (DE); Georg Passig, Koesching (DE); Robert Haslinger, Groebenzell (DE); Andreas Tobergte, Munich (DE); Ulrich Seibold, British Columbia (CA)

(73) Assignee: Deutsches Zentrum fur Luft-und Raumfahrt E.V., Cologne (DE)

( * ) Notice: Subject to any disclaimer, the term of this patent is extended or adjusted under 35 U.S.C. 154(b) by 209 days.

(21) Appl. No.: 13/580,612

(22) PCT Filed: Feb. 17, 2011

(86) PCT No.: PCT/EP2011/052360
§ 371 (c)(1),
(2), (4) Date: Aug. 22, 2012

(87) PCT Pub. No.: WO2011/104165
PCT Pub. Date: Sep. 1, 2011

(65) Prior Publication Data
US 2012/0316681 A1    Dec. 13, 2012

(30) Foreign Application Priority Data
Feb. 23, 2010  (DE) .................. 10 2010 009 065

(51) Int. Cl.
| | |
|---|---|
| G05B 19/00 | (2006.01) |
| G06F 3/01 | (2006.01) |
| G06F 3/0346 | (2013.01) |
| G05B 15/00 | (2006.01) |
| A61B 19/00 | (2006.01) |
| A61B 17/00 | (2006.01) |

(52) U.S. Cl.
CPC .......... *G06F 3/014* (2013.01); *A61B 2019/2223* (2013.01); *A61B 19/2203* (2013.01); *A61B 2019/2269* (2013.01); *A61B 2017/00207* (2013.01); *A61B 2019/467* (2013.01); *G06F 3/0346* (2013.01); *A61B 2017/00221* (2013.01); *A61B 2019/5259* (2013.01)
USPC .......................... 700/258; 700/250; 700/252

(58) Field of Classification Search
USPC .................................. 700/245, 248, 250, 252
See application file for complete search history.

(56) References Cited

U.S. PATENT DOCUMENTS

| | | |
|---|---|---|
| 5,389,849 A | 2/1995 | Asano et al. |
| 5,876,325 A | 3/1999 | Mizuno et al. |

(Continued)

FOREIGN PATENT DOCUMENTS

DE   10 2007 022120 A1   11/2008

OTHER PUBLICATIONS

International Search Report dated May 27, 2011, as issued in International Patent Application No. PCT/EP2011/052360, filed Feb. 17, 2011.

*Primary Examiner* — Ian Jen
(74) *Attorney, Agent, or Firm* — Maier & Maier, PLLC

(57) ABSTRACT

The input apparatus (1) for medical minimally invasive robots or medical simulators consists of at least one handheld device (10) having a first operating part (12) and a second operating part (14), wherein the first and second operating parts (12,14) are connected to one another via a pivot joint (16), a measuring system (20) having one or more sensors for determining an angle between the first and second operating parts (12,14), for contactlessly detecting the spatial position of the handheld device and for contactlessly detecting the orientation of the handheld device, and a computer unit (22) which can be connected to the handheld device (10) via a data link.

15 Claims, 2 Drawing Sheets

(56) References Cited

U.S. PATENT DOCUMENTS

| | | |
|---|---|---|
| 7,236,618 B1 | 6/2007 | Chui et al. |
| 2007/0005187 A1 | 1/2007 | Bellanger |
| 2009/0213073 A1* | 8/2009 | Obermeyer et al. .......... 345/161 |
| 2010/0013764 A1 | 1/2010 | Gu et al. |
| 2010/0021378 A1* | 1/2010 | Rousso et al. ................ 424/1.11 |
| 2013/0116707 A1* | 5/2013 | Seibold et al. ................ 606/130 |

\* cited by examiner

INPUT APPARATUS FOR MEDICAL MINIMALLY INVASIVE ROBOTS OR MEDICAL SIMULATORS AND MEDICAL DEVICE HAVING AN INPUT APPARATUS

RELATED APPLICATIONS

This is the U.S. national stage application which claims priority under 35 U.S.C. §371 to International Patent Application No.: PCT/EP2011/052360 filed on Feb. 17, 2011, which claims priority to German Patent Application No. 10 2010 009 065.4 filed on Feb. 23, 2010, the disclosures of which are incorporated by reference herein their entireties.

The invention relates to an input apparatus for medical minimally invasive robots or medical simulators and to a medical device having such an input apparatus.

With minimally invasive robot systems or corresponding simulators, input apparatuses or devices are needed that detect the movements of a surgeon's hands and transfer them to the corresponding real or virtual instruments. Here, the surgeon sits at a console, where the surgery process inside the patient is visualized by video.

For a bimanual remote control of minimally invasive robot systems or corresponding simulators, haptic input apparatus are known, for example. These are cinematic input apparatus which mostly comprise a mechanical system with a handle or a finger receptacle and are arranged stationarily with their base. By moving the hands, sensor values are generated in this mechanical system, which are used to calculate the movements made by the user. The mechanical systems may be, for example, a passive robot arm, in which the movements of the robot are calculated from the joint angles. Such an input apparatus is known, for example, from US 2007/0005187 A1.

Further, contactlessly detected passive handheld apparatuses are known. From DE 10 2007 022 120 A1, for example, a grip operating device is known comprising a ball body to be enclosed by a surgeon's fingers and a movable forefinger lever guided at the ball body, where an optical tracking element is provided at the ball body that detects the position of the grip operating device by means of a stationary camera.

Moreover, a contactlessly detected data glove is known as an input apparatus from U.S. Pat. No. 7,236,618 B1.

With the above described haptic input apparatus, the mass, the inertia and the friction of the mechanical components have to be compensated, so that working at these input apparatus for longer periods leads to operator fatigue.

The instruments that a surgeon primarily controls remotely are most often forceps, scissors, pincers or the like.

However, an intuitive operation of these instruments is not possible using the known contactlessly detected handheld devices. The surgeon operating such a device thus has to learn anew how to operate such an input apparatus for the instruments.

Therefore, it is an object of the present invention to provide an input apparatus for operating a manual remote control of minimally invasive robot systems or corresponding medical simulators, which allows for an intuitive operation of the remote-controlled instruments. The input apparatus shall be robust and avoid the disadvantages of the haptic input apparatus.

The object is achieved with the features of claim 1.

The invention provides an input apparatus for medical minimally invasive robot or medical simulators comprising at least one handheld device with a first operating part and a second operating, where the first operating part and the second operating part are connected via a pivot joint, and a computer unit adapted to be connected with the handheld device via a data link.

The input apparatus further comprises a measuring system comprising one or a plurality of sensors for determining an angle between the first and the second operating part for contactlessly detecting the spatial positions of the handheld device, as well as for contactlessly detecting the orientation of the handheld device.

The first and the second operating parts are articulately connected via the pivot joint so that the angle between the first and the second operating part is variable. The first and the second operating part can thus perform a movement that simulates the movement of forceps, scissors, pincers and the like.

By means of the sensors that detect or determine the angle between the first and the second operating part, the spatial position of the handheld device and the orientation of the handheld device, these data can be used to control the robot or the simulator, and the movement made by the first and the second operating part can be performed by a corresponding medical instrument or the corresponding simulator. This allows for an intuitive operation of such a robot or simulator via the input apparatus of the invention.

By the fact that the sensors detect the spatial position of the handheld device and the orientation of the hand held device in a contactless manner, it is further prevented that an operator experiences signs of fatigue due to operating the input apparatus of the invention. The operator can move the handheld devices freely in space so that a particularly advantageous operation is possible.

It is possible due to the invention that, for example, the first and the second operating part of a handheld device are connected such that in a closed position of the handheld device, the first operating part and the second operating part overlap at least in part. Thus, it is possible, for example, by the movement of the first and the second operating part, to simulate the movement of the legs of a pair of scissors. When the input apparatus of the invention operates a minimally invasive robot with a scissors- or forceps-like instrument, for example, a particularly good operation is possible, since each handheld device performs movements that are almost identical with those of the corresponding instrument. Of course, it is also possible that the first and the second operating part do not overlap, but abut on each other in parallel, when the handheld device is in the closed position.

In an embodiment of the invention it is advantageously provided that electronics are arranged in at least one of the operating parts, which at least partly from the measuring system, the electronics preferably comprising at least a sensor for measuring the angle between the first and the second operating part, at least one acceleration sensor for detecting the translational acceleration of the handheld device and/or at least one rotation speed sensor for detecting the rotation rates of the handheld device.

By providing electronics in one of the operating parts, which at least partly from the measuring system, the angle, the spatial position of the handheld device and/or the orientation of the handheld device can be detected in a particularly advantageous manner, since the measurement is performed directly at the device. Further, the input apparatus can be designed in a very compact manner, since at least a part of the measuring system is already arranged in the handheld device.

Preferably, it is provided that the operating part comprises a support surface for fingers, each support surface preferably being provided with one or more fastening loops. This allows the user to hold and operate the handheld device with the fingers in an advantageous manner. The fastening loops further allow the handheld device to be fixed to the fingers of the user so that the handheld device is prevented from slipping from the user's hands.

Here, it may advantageously be provided that a sensor for detecting the presence of a finger is provided at at least one of the support surfaces. By means of the sensor for detecting the presence of a finger, it is possible, for example that only those handheld devices that are gripped by a user's hand at all or in a correct manner, are used in operating the robot or the medical simulator.

In an embodiment of the invention it may be provided that a spring element is arranged at the pivot joint, which exerts a spring force on the first and second operating part, such that the first and the second operating part are biased to an initial position. The initial position may be an open position of the handheld device wherein the first and the second operating part are arranged under a certain angle with respect to each other.

By providing a spring element, it is achieved that, when operating the handheld device, the initial position of the first and the second operating part is reached in a simple manner without the operator having to exert any force.

Thereby, the control of the robot or the simulator via the handheld device of the invention can be performed in an advantageous manner. The spring element provides the handheld device of the invention with characteristics that are adequate to those of real pincers so that especially when controlling a robot with pincers as the instrument, the handheld device of the invention allows a particularly realistic handling.

It may be provided that one or each handheld device comprises at least one motor that generates vibrations and/or acceleration impulses along one or a plurality of spatial axes and/or exerts a torque on the first and the second operating part. In this manner, it becomes possible to exert impulses on the handheld device that are suited to transmit information to the user. For example, when gripping an object, the pressure exerted on that object can be transmitted to the handheld device of the input apparatus via the motor so that the operator senses that he has gripped an object by means of the medical robot.

The at least one sensor for measuring the angle between the first and the second operating part may be a potentiometer or an optical distance sensor, for example. The acceleration sensor for the detection of the translational acceleration of the handheld device may be an acceleration sensor in MEMS technology, for example.

The rotation speed sensor for the detection of the handheld device may be a rotation rate sensor, for example, based on the gyroscopic principle, preferably a micromechanical gyroscope.

The data link between the computer unit and the handheld device may be a wire link or a wireless data link.

In addition or as an alternative to one or a plurality of sensors integrated in the handheld device for the detection of the spatial position of the handheld device and of the orientation of the handheld device, it may be provided that the input apparatus of the invention comprises a position sensor that measures the distance between the handheld device and a stationary reference, the measurement preferably being an optical measurement and the position sensor preferably being arranged in the handheld device, preferably in the first or the second operating part.

In this manner, the position and the orientation of the handheld device can be determined in general or, when the position sensor is used as an additional sensor, more exactly. Thereby, a translational drift of the sensors can be compensated, for example.

In addition or as an alternative it may be provided that at least one emitter arranged in the handheld device, for example in the first or the second operating part, and a position measuring sensor system are provided, the system detecting the spatial position and/or the spatial orientation of the handheld device and/or of the first and second operating part through the at least one emitter. This system can form the measuring system of the invention in its entirety or may serve as an additional system for the exact detection of the desired data.

In the context of this invention, the term emitter refers to both active systems that emit light, for instance, and passive systems that only reflect light, for instance.

The position measuring sensor system may comprise an optical camera system, the at least one emitter being at least one passive marker, preferably a pattern, and/or at least one active marker, preferably in the form of luminous elements such as infrared light emitting diodes, for instance.

It may also be provided that the at least one emitter builds up an electromagnetic field that is detected by the position measuring sensor system. The spatial position and/or the spatial orientation of the handheld device and/or the operating parts can be determined from the orientation of the magnetic lines of the electromagnetic field.

The invention further provides a medical apparatus with an input apparatus of the invention, preferably with two handheld devices.

The following is a detailed description of the invention with reference to the following drawing. In the Figures:

FIG. 1 illustrates a first embodiment of an input apparatus 1 of the invention comprising two handheld devices 10 for operating a medical minimally invasive robot or a medical simulator in use.

Figure 2:
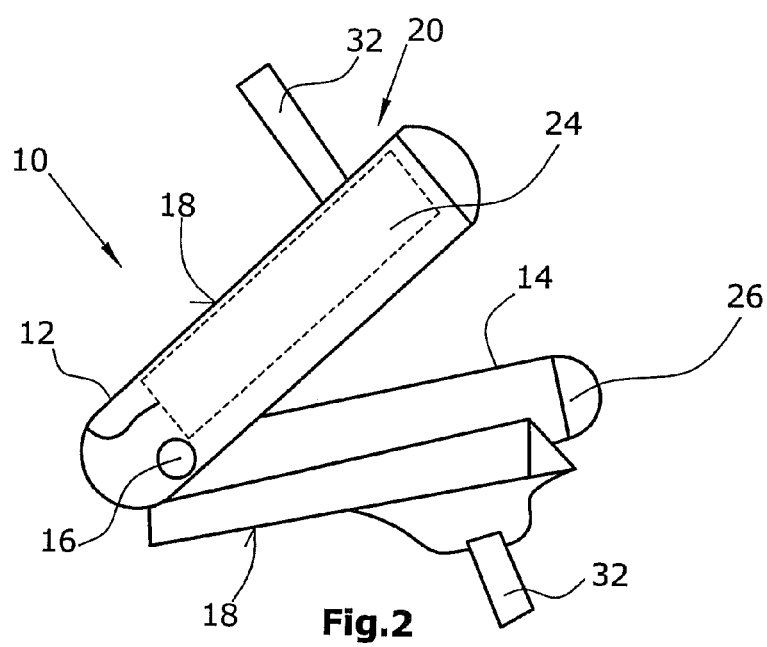
FIG. 2 is a schematic illustration of a handheld device of an input apparatus of the invention.

Each handheld device 10 comprises, as best seen from FIG. 2, a first operating part 12 and a second operating part 14. The first and the second operating part 12, 14 are connected via a pivot joint 16.

On the side respectively averted from the other operating part, the first and the second operating part 12, 14 each have a support surface 18 for fingers so that the handheld device 10 can be gripped by the user with two or more fingers.

For the operation of the medical minimally invasive robot or the medical simulator, the operator can move the handheld devices freely in space and varies the angle between the first operating part 12 and the second operating part 14 by exerting pressure on the support surfaces 18. A measuring system 20 detects the spatial position of each handheld device 10 and the orientation of each handheld device 10, as well as the angle between the first operating part 12 and the second operating part 14.

The data detected are transmitted to a computer unit 22 that calculates the corresponding movement of the minimally invasive robot or the medical simulator from the data. In the embodiment illustrated in FIG. 1, the data are transmitted wirelessly.

For the determination of the movements of each handheld device 10, the measuring system 20 comprises one or a plurality of sensors that acquire the corresponding data. For this purpose, the handheld device 10 may comprise the electronics 24 schematically illustrated in FIG. 2. The electronics 24 may comprise a part or all of the measuring system 20. In the embodiment in which the electronics 24 comprises all of the measuring system 20, the electronics include one or a plurality of sensors for measuring the first and the second operating part 12, 14, one or a plurality of acceleration sensors for detecting the translational acceleration of the handheld device 10, and one or a plurality of rotation speed sensors for detecting the rotation speed of the handheld device 10. Here, a sensor for measuring the angle between the first operating part 12 and the second operating part 14 can be a potentiometer or an optical distance sensor. An acceleration sensor for detecting the translational acceleration of the handheld device 10 may be an acceleration sensor with MEMS technology (Micro-Electro-Mechanical Systems). A rotation speed sensor for detecting the rotation speed of the handheld device 10 may be a rotation rate sensor based on the gyroscopic principle, e.g. a micromechanical gyroscope.

Of course, it is also possible that the electronics 24 only form a part of the measuring system 20 and only comprises, for example, one or a plurality of sensors for measuring the angle between the first operating part 12 and the second operating part 14. In this case, the detection of the spatial position of the handheld device 10 and the detection of the orientation of the handheld device 10 is effected via external sensors, for instance. The electronics 24 further comprises an interface for data transmission to the computer unit 22.

It is further possible that each handheld device 10 comprises one or a plurality of position sensors 26 that measure the position and the orientation of the handheld device 10 with respect to a stationary reference 28. For example, the measuring can be done optically. In this case, the position sensor 26 and the stationary reference 28 form a part of the measuring system 20. It is further possible that the at least one position sensor 26 and the stationary reference 28 are provided in addition to at least one acceleration sensor and rotation speed sensor provided in each handheld device 10, so that a translational drift of the other sensors can be compensated, for example, by the additional data acquired by the at least one position sensor.

Figure 3:
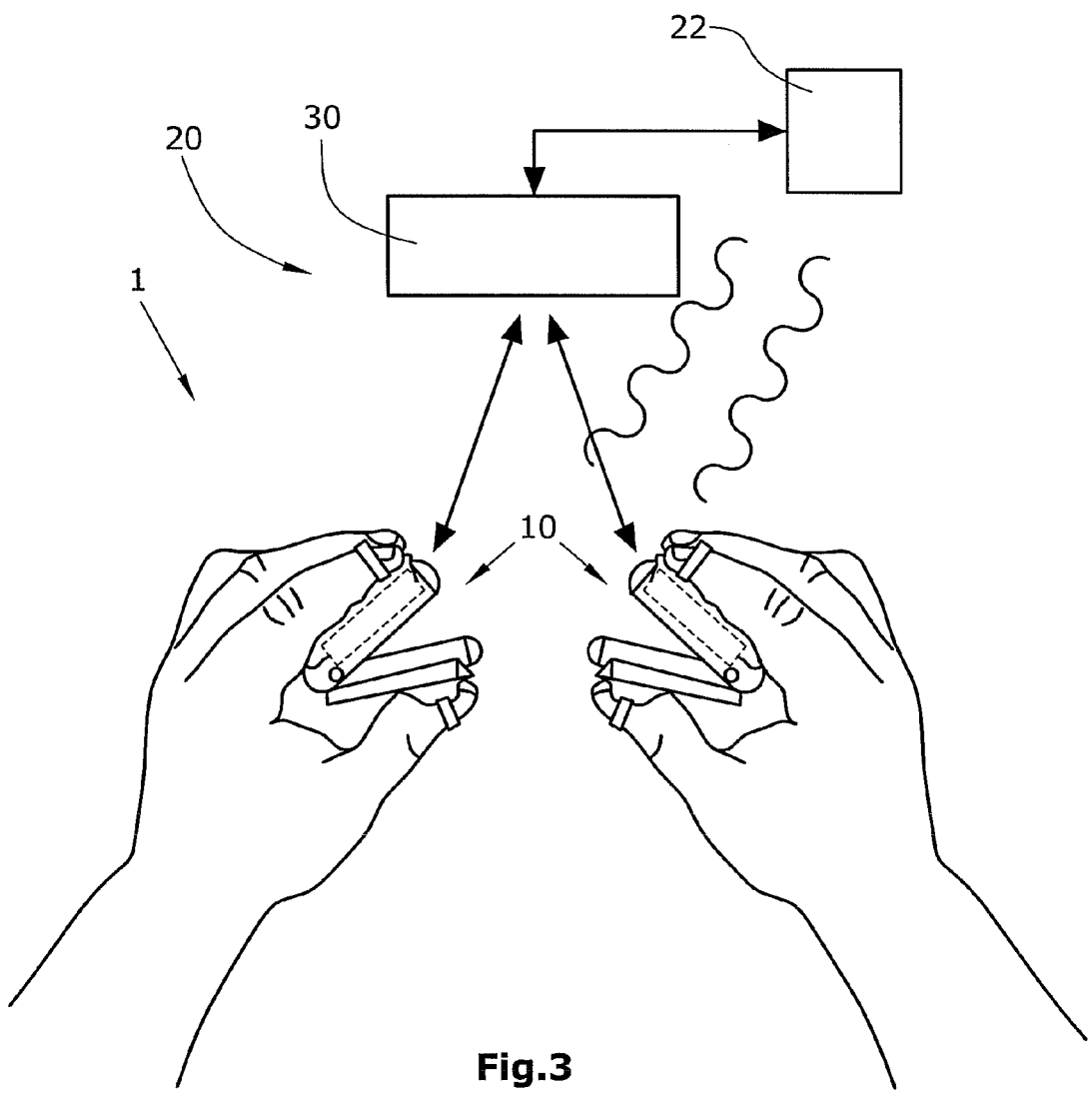
FIG. 3 is a schematic illustration of a second embodiment of an input apparatus comprising two handheld devices.

FIG. 3 schematically illustrates a second embodiment of an input apparatus 1 of the invention comprising two handheld devices 10.

Figure 1:
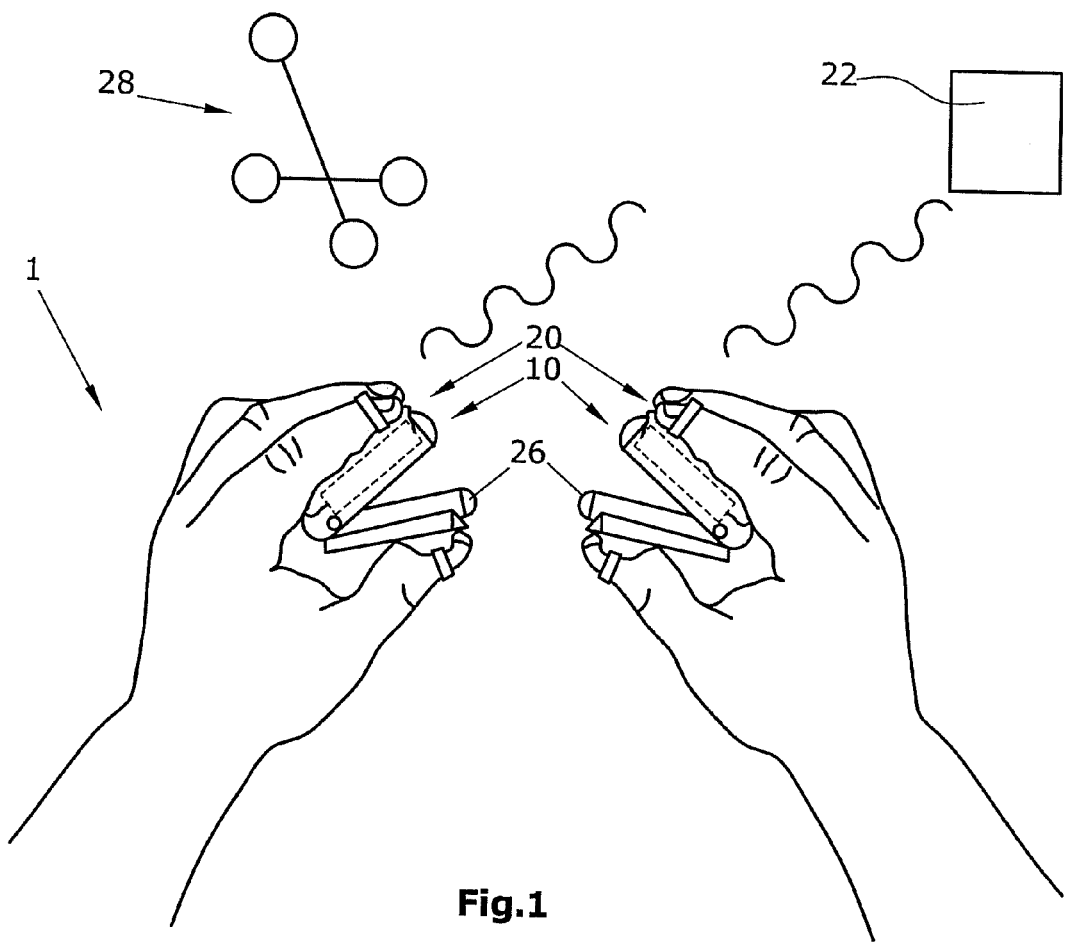
FIG. 1 is a schematic illustration of a first embodiment of an input apparatus of the invention comprising two handheld devices, the device being shown in use.

The input apparatus 1 illustrated in FIG. 3 differs from the input apparatus 1 of the invention illustrated in FIG. 1 substantially in that an emitter, not illustrated in FIG. 3, is arranged at each handheld device 10 and that a position measuring sensor system 30 is provided that is connected with the computer unit 22. Here, the emitter of the handheld devices 10 and the position measuring sensor system 30 form a part of the measuring system 20. Via the position measuring sensor system 30 and each emitter of the handheld devices 10, the spatial position and/or the spatial orientation of each handheld device 10 and/or each first and second operating part 12, 14 can be detected. The position measuring sensor system 30 may be formed by an optical camera system, for example, and each emitter can be at least one passive or at least one active marker at the handheld device 10. For example, a passive marker is a pattern provided on the handheld device 10 which is detected by the optical camera system. Luminous elements, such as infrared light emitting diodes could be used as active markers, for example. The light emitted by the luminous elements is captured by the optical camera system to detect the spatial position and the spatial orientation of the handheld device.

It is also possible that the emitters arranged at the handheld device 10 build up an electromagnetic field and that the position measuring sensor system 30 measures the orientation of the magnetic lines of the electromagnetic field. In this manner, it is possible to detect the spatial position and/or the spatial orientation of the handheld device and/or the first and second operating part 12, 14.

The above described system of emitter and position measuring sensor system may again be provided as an alternative or in addition to sensors provided in the handheld device 10.

According to an embodiment not illustrated it is also possible that at least one emitter is provided at the first operating part 12 and the second operating part 14, respectively, so that the position of the first operating part 12 and the second operating part 14 is detected via the position measuring sensor system 30. In this manner, the angle between the first operating part 12 and the second operating part 14 can be detected using such a system.

As is seen best in FIG. 2, the first operating part 12 and the second operating part 14 may each comprise fastening loops 32 on the support surface 18 that allows for a fixation of the handheld device 10 at the hand of the user. It is thus avoided that the handheld device 10 slips from the user's hand during use. Moreover, the fastening loops 32 allow the user to move the handheld device 10 from a closed position to an open position.

The support surfaces 18 may be provided with sensors for detecting the presence of a finger. Thereby, it becomes possible that a handheld device 10 is activated only in the presence of a finger on the support surface 18, for example.

Further, non-illustrated energy storages can be provided in the handheld device 10 that supply the necessary energy to the electronics 24.

The pivot joint 16 may be designed as a pivot pin hinge or as an elastic joint in the form of a film hinge.

The first operating part 12 and the second operating part 14 of a handheld device 10 can be connected such that, in the closed position of the handheld device 10, the first operating part 12 and the second operating part 14 overlap at least partly. Thus, the movement of the first and the second operating part 12, 14 simulates the movement of the legs of a pair of scissors. If the input apparatus 1 of the invention controls a minimally invasive robot with a scissors- or forceps-like instrument, this arrangement allows for a particularly favorable handling, since each handheld device 10 performs almost the same movement as the corresponding instrument.

Of course, it is also possible that the first and the second operating part 12, 14 do not overlap, but abut against each other in parallel when in the closed position.

A spring element, not illustrated in FIG. 2, may be arranged at the pivot joint 16, which spring element exerts a spring force on the first operating part 12 and the second operating part 14 such that the first operating part 12 and the second operating part 14 are biased into an initial position. The initial position may be the position illustrated in FIG. 2, for example. The spring element exerting a corresponding force makes it possible to return the handheld device 10 into the initial position. Thus, the handheld device 10 can be operated in a manner comfortable to the user.

Further, each handheld device 10 may be provided with a motor generating vibrations and/or acceleration impulses along one or a plurality of spatial axes and/or a torque on the first and the second operating part. In this manner, information can be presented to the user in a haptic manner. By exerting a torque on the first and the second operating part 12, 14, a force feedback to the user can be generated. The force feedback may, for example, realistically simulate the gripping of an object with the instrument of the minimally invasive robot, by making the user feel a corresponding counterforce at the handheld device 10.

Using the input apparatus of the invention allows for a particularly simple and advantageous operation of a medical minimally invasive robot or medical simulator, since the handheld device either simulates the movement of the corresponding instrument itself or the movement of a handle part of a conventional instrument. Thus, a particularly simple and intuitive handling is possible, without the user having to learn the movement sequences anew.

The invention claimed is:

1. An input apparatus for medical minimally invasive robots or medical simulators comprising:
   at least one handheld device having a first operating part and a second operating part, wherein the first and second operating parts are connected to one another via a pivot joint,
   a measuring system having one or more sensors for determining an angle between the first and second operating parts, for contactlessly detecting the spatial position of the handheld device and for contactlessly detecting the orientation of the handheld device, and
   a computer unit which can be connected to the handheld device via a data link.

2. The input apparatus of claim 1, wherein electronics are arranged in at least one of the operating parts, which form at least a part of the measuring system, wherein the electronics preferably comprise a sensor for measuring the angle between the first and the second operating part, an acceleration sensor for detecting the translational acceleration of the handheld device and a rotation speed sensor for detecting the rotation speed of the handheld device.

3. The input apparatus of claim 1, wherein each operating part has a support surface for fingers, wherein one or a plurality of fastening loops is provided on each support surface.

4. The input apparatus of claim 3, wherein a sensor for detecting the presence of a finger is provided at at least one support surface.

5. The output device of claim 1, wherein a spring element is arranged at the pivot joint, which spring element exerts a spring force on the first and second operating parts such that the first and second operating parts are biased into an initial position.

6. The input apparatus of claim 1, wherein one or each handheld device comprises at least one motor that generates vibrations and acceleration impulses along one or a plurality of spatial axes of the handheld device and/or exerts a torque on the first and second operating parts.

7. The input apparatus of claim 2, wherein the at least one sensor for measuring the angle between the first and second operating parts is a potentiometer or an optical distance sensor.

8. The input apparatus of claim 2, wherein the acceleration sensor for detecting the translational acceleration of the handheld device is an acceleration sensor in MEMS technology.

9. The input apparatus of claim 1, wherein the rotation speed sensor for detecting the rotation speed of the handheld device is a rotation rate sensor based on the gyroscopic principle, preferably a micromechanical gyroscope.

10. The input apparatus of claim 1, wherein the data link between the computer unit and the handheld device is a wire or a wireless data link.

11. The input apparatus of claim 1, wherein the position sensor that measures the distance between the handheld device and a stationary reference, the measuring preferably being performed optically, and the position sensor preferably being arranged in the handheld device, preferably in the first or the second operating part.

12. The input apparatus of claim 1, wherein at least one emitter arranged in the handheld device, preferably in the first or the second operating part, and by a position measuring sensor system that detects the spatial position and the spatial orientation of the handheld device and/or the first and second operating parts via the at least one emitter.

13. The input apparatus of claim 12, wherein the position measuring sensor system comprises an optical camera system and the at least one emitter comprises at least one passive marker, preferably a pattern, and at least one active marker, preferably in the form of luminous elements.

14. The input device of claim 12, wherein an electromagnetic field can be built up via the at least one emitter, said electromagnetic field being detected by the position measuring sensor system.

15. A medical apparatus comprising an input apparatus of claim 1, preferably comprising two handheld devices.

* * * * *